(12) United States Patent
Squirrell

(10) Patent No.: US 7,638,097 B2
(45) Date of Patent: Dec. 29, 2009

(54) REAGENT DELIVERY SYSTEM

(75) Inventor: David James Squirrell, Salisbury (GB)

(73) Assignee: The Secretary of State for Defence (GB)

( * ) Notice: Subject to any disclaimer, the term of this patent is extended or adjusted under 35 U.S.C. 154(b) by 918 days.

(21) Appl. No.: 10/476,278

(22) PCT Filed: Apr. 18, 2002

(86) PCT No.: PCT/GB02/01797

§ 371 (c)(1),
(2), (4) Date: Apr. 21, 2004

(87) PCT Pub. No.: WO02/087762

PCT Pub. Date: Nov. 7, 2002

(65) Prior Publication Data

US 2004/0209266 A1 Oct. 21, 2004

(30) Foreign Application Priority Data

Apr. 30, 2001 (GB) .................................. 0110476.9

(51) Int. Cl.
*B01L 3/02* (2006.01)
(52) U.S. Cl. .................. 422/100; 422/61; 436/180; 435/287.3
(58) Field of Classification Search ............. 435/287.3; 422/61, 100; 436/180
See application file for complete search history.

(56) References Cited

U.S. PATENT DOCUMENTS

| | | | |
|---|---|---|---|
| 3,893,470 A | 7/1975 | MacPhee et al. | |
| 4,942,017 A | 7/1990 | Turpen | |
| 4,980,293 A | 12/1990 | Jeffs | |
| 5,229,297 A * | 7/1993 | Schnipelsky et al. | 436/94 |
| 5,320,808 A * | 6/1994 | Holen et al. | 422/64 |
| 5,462,881 A | 10/1995 | Perlman | |
| 5,652,143 A | 7/1997 | Gombrich et al. | |
| 6,040,192 A * | 3/2000 | Tuunanen | 436/177 |
| 6,436,355 B1 * | 8/2002 | Lee et al. | 422/199 |
| 6,514,461 B1 * | 2/2003 | Lappe et al. | 422/68.1 |

FOREIGN PATENT DOCUMENTS

| | | |
|---|---|---|
| EP | 0296700 | 12/1988 |
| EP | 0339277 | 11/1989 |
| WO | WO 80/02205 | 10/1980 |
| WO | WO 98/13684 | 4/1998 |
| WO | WO 98/24548 | 6/1998 |

* cited by examiner

*Primary Examiner*—Lyle A Alexander
*Assistant Examiner*—Dennis M White
(74) *Attorney, Agent, or Firm*—Dean W. Russell; Kristin M. Crall; Kilpatrick Stockton LLP

(57) ABSTRACT

A delivery apparatus for selectively delivering one or more liquid reagents into a reaction or test chamber (2), especially of an assay apparatus, the apparatus comprising: one or more respective storage chambers (5,6) for containing the one or more liquid reagents and arranged generally above the reaction or test chamber (2); and a plunger element (4) arranged and operable for insertion into the mouth of a selected storage chamber so as to displace a selected reagent from therewithin into the reaction or test chamber (2) generally therebelow by gravitational liquid overflow from the mouth of the chamber. The apparatus may conveniently be provided as a discrete delivery unit, with the storage chambers (5,6) prefilled with the selected reagents.

25 Claims, 5 Drawing Sheets

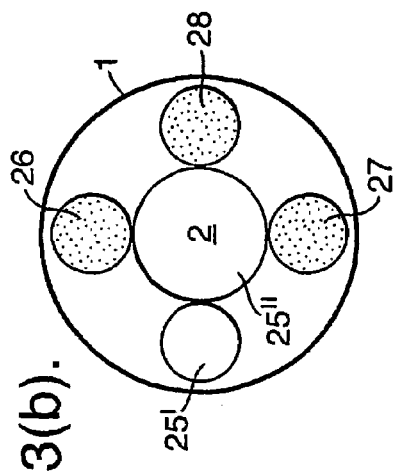
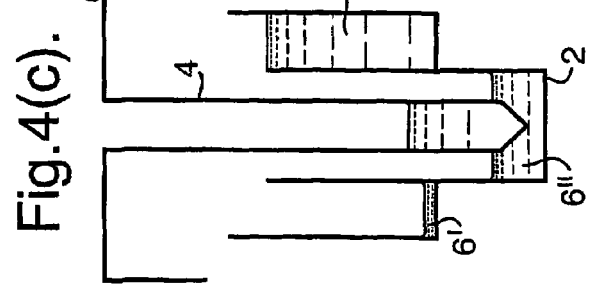
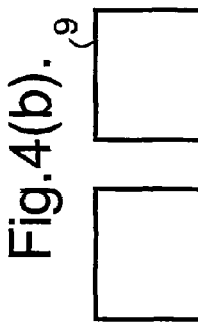
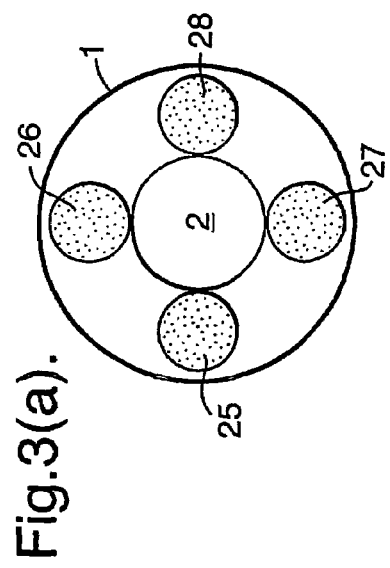
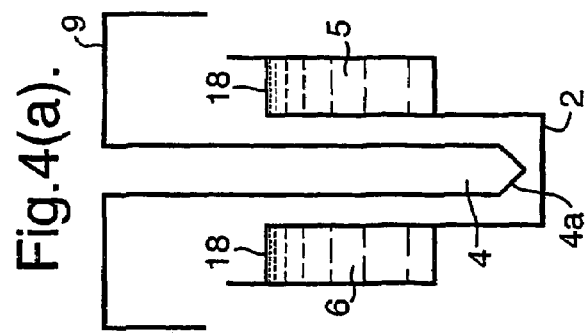

Fig.5(a).
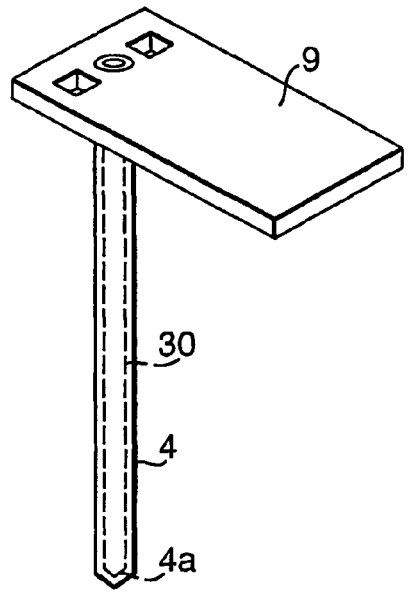
Fig.5(b). Fig.5(c). Fig.5(d).
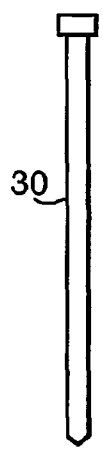 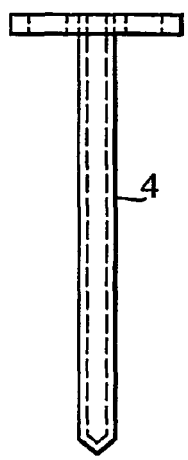 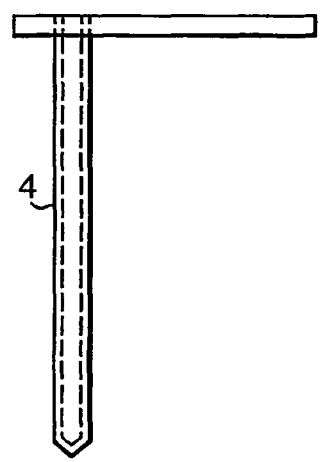
Fig.5(e).
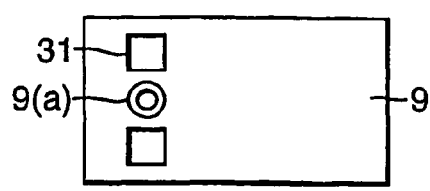

REAGENT DELIVERY SYSTEM

CROSS-REFERENCE TO RELATED APPLICATIONS

This application is the U.S. national phase of International Application No. PCT/GB02/01797 filed on Apr. 18, 2002 and published in English as International Publication No. WO 02/087762 A1 on Nov. 7, 2002, which application claims priority to Great Britain Application No. 0110476.9 filed on Apr. 30, 2001, the contents of which are incorporated by reference herein.

This invention relates to a reagent delivery system, more particularly to an apparatus for selectively delivering one or more liquid reagents into a reaction or test chamber of for example an assay apparatus. The invention also relates to a discrete reagent delivery unit for use therein, as well as to a method for delivering one or more liquid reagents to a reaction or test chamber in such an apparatus.

Many biochemical reaction procedures, such as the extraction and purification of DNA or the detection of microorganisms, require the sequential addition of one or more (typically a plurality of) reagents, to a reaction or test chamber, often in accurately measured and/or timed amounts, and which reagents must be kept separate prior to use. However, given this requirement for separate storage prior to delivery, it is difficult to provide for selective delivery of each reagent in accurately measured and/or timed amounts utilising an apparatus that is simple, compact and cost-effective. These conflicting criteria are made all the more difficult to realise practically and commercially in the context of an automated test or assay apparatus, where it is desirable that set-up procedures are simplified and overall cost, system maintenance and operator involvement are minimised.

Although there are many known commercial examples of test or assay apparatuses incorporating various types of reagent delivery system, most if not all are deficient in at least one or some of the above-mentioned criteria.

In a first aspect the present invention provides a delivery apparatus for selectively delivering one or more liquid reagents into a reaction or test chamber, the apparatus comprising:

one or more respective storage chambers for containing the one or more liquid reagents and arranged generally above the reaction or test chamber; and a plunger element arranged and operable for insertion into the mouth of a selected storage chamber so as to displace a selected reagent from therewithin into the reaction or test chamber generally therebelow by gravitational liquid overflow from the mouth of the chamber.

Embodiments of the apparatus of the invention provide a reagent delivery system which allows for separate reagent storage prior to use, together with accuracy of dosed amounts and/or times as and when desired, yet utilising an apparatus which may be cheap, compact and simple to set up, use and maintain.

The underlying principle of apparatus embodying the invention has been found to be the use of a plunger inserted into a liquid reagent-containing storage chamber to cause displacement of the reagent so that it overflows from the storage chamber mouth and flows under gravity into a reaction or test chamber arranged generally below the storage chamber.

In preferred practical embodiments of this first aspect of the invention the delivery apparatus forms part of a reaction, test or assay apparatus, especially an automated one, which comprises the said reaction or test chamber, the said one or more respective storage chambers arranged generally thereabove and the said plunger element, together with control means for controlling physical movement of the plunger element.

The apparatus may further comprise heating means arranged to control the temperature of reagents within the said reaction or test chamber and/or the one or more storage chambers. The heating means suitably comprises an electrically conducting polymer as described in more detail below, which is heatable by means of passing a controlled electric current through it. Thus the apparatus may further comprise control means such as computer control means, for the heating means.

The control means will preferably generally comprise mechanical means for engaging and physically moving the plunger, such as are well known in existing test or assay machines, and appropriate hardware and software programmed to effect predetermined movements of the plunger element according to whatever reaction, test or assay procedure(s) is/are to be effected using the apparatus. More will be said about this further below.

The delivery apparatus of this first aspect of the invention may for example be employed in a final stage of a multi-stage assay apparatus, e.g. for carrying out adenylate kinase (AK) amplification assays for detecting bacterial contamination of food, in which several reagents are required to be sequentially delivered to a test chamber containing a pre-prepared sample for the purpose of AK-phage endpoint analysis. An example of such an assay technique is described in EP-A-0 680 515. As another example, this delivery apparatus could be employed as a discrete stage in the extraction and purification of DNA, where sequential delivery of several different reagent liquids to a single reaction vessel is required.

In practical terms, use of the above-defined delivery apparatus in either of the above exemplary cases may be made all the more expedient by providing the reaction or test chamber and the one or more reagent storage chamber(s) as a unitary, discrete unit.

Accordingly, in a second aspect the invention provides a reaction or test unit including a reaction or test chamber, for use in a reaction or test procedure in which one or more liquid reagents are selectively delivered into the reaction or test chamber, the unit further comprising one or more respective storage chambers for containing the one or more liquid reagents, wherein the one or more storage chambers have closed bottoms, openable or open mouths and are arranged generally above the reaction or test chamber.

If desired the test chamber and/or the storage chamber may be supplied with heating and/or cooling means. Where the test chamber is provided with such means, it is possible to readily conduct reactions within the test chamber that require heating or cooling or thermal cycling, such as amplification reactions, for instance the polymerase chain reaction (PCR). Where the storage chambers are provided with heating and/or cooling means, these may be employed to allow reagents to be delivered to the test chamber at a particular temperature.

In particular, the heating means comprises an electrically conducting polymer, for example as described in WO 98/24548. The polymer heats when an electric current is passed through it. However, the low thermal mass of the polymer means that rapid cooling can also be assured when the current is off.

These polymers are flexible and convenient, as they may be folded or shaped to make intimate contact with any reaction vessel including test and/or storage chambers of the present invention. Thus, the polymer may form for example a sheath around the test and/or storage chambers, or it may be integral with it.

Where the test chamber and/or the storage chambers include electrically conducting polymers as an integral part thereof, they may be made from the polymer by extrusion, injection moulding or similar techniques. Alternatively, the test chamber or storage chamber may be manufactured using a composite construction in which a layer of the conducting polymer is interposed between layers of the material from which the vessel is made or in which the internal or external surfaces of the reaction vessel is coated with the polymer, or again in which the vessel is basically made of the polymer coated with a thin laminate of a PCR compatible material. Such vessels may be produced using lamination and/or deposition such as chemical or electrochemical deposition techniques as is conventional in the art.

In a particular embodiment however, the test and/or storge chambers have electrically conducting polymer integral only with a particular region of the test or storage chambers, and in particular a lower region where reagents are contained or stored. This provides for efficient heating just of the reagents and not of other regions of the chambers. Such chambers may be produced using conventional "overmoulding" techniques.

Test or storage chambers which comprise the polymer as an integral part may provide particularly compact structures.

In preferred practical embodiments of this second aspect of the invention the reaction or test chamber and the one or more storage chambers are formed of, and preferably contained within an integral housing of, a suitable moulded plastics material, e.g. polypropylene. The housing may preferably include an upper peripheral wall which collectively surrounds and extends upwardly past the mouths of the storage chambers in order to act as a baffle to direct liquid reagents overflowing from the chambers into the reaction or test chamber therebelow.

Where the test or storage chambers include electrically conducting polymers, the housing may be provided with electrical contacts, arranged to contact the electrically conducting polymer heating means when the test or storage chambers are in position in the housing. These contacts are suitably connected to an electrical supply, preferably by way of an automatic controller such as a computer, so that the temperatures of the reagents within the test or storage chambers can be controlled automatically. If necessary, a temperature monitoring device such as a thermocouple may also be included and the results may be fed back to the control means so as to ensure that the desired temperatures are accurately achieved and/or maintained.

The unit may conveniently be provided with the one or more storage chambers prefilled with selected reagents in predetermined amounts and the mouths of the chamber(s) suitably sealed with puncturable sealing means, such as conventional foil seals. The reaction or test chamber of the unit may be provided empty or may contain a predispensed amount of a solid (eg. freeze-dried) or liquid reagent with the chamber being likewise sealed with its own corresponding protective seal.

Furthermore, there may if desired be provided below the reaction or test chamber an auxiliary reagent chamber whose mouth is itself sealed with a corresponding protective seal which defines the bottom of the reaction or test chamber, which auxiliary chamber contains a predispensed amount of an auxiliary liquid or solid reagent into which the contents of the reaction or test chamber may be delivered at a desired stage in the overall procedure. In some cases, the auxiliary reagent chamber may be suspended above the bottom of the reaction or test chamber. This allows yet further reagents to be contained at the bottom of the test chamber, which will be included in the reaction only when both the upper and lower surfaces of the reagent chamber are perforated.

Preferably the sealing means closing each of the aforementioned chambers of the unit will be readily breakable or perforatable by the tip of the plunger element as it moves into a respective chamber's mouth. Preferably, therefore, the tip of the plunger element is appropriately shaped for this purpose. It may for example be conical, with a sharp tip and/or it could for instance be formed with buttresses or ribs on its outer surface. In certain embodiments the tip portion of the plunger may even have one or more channel formations formed in its outer surface as a route for liquid reagent to drain therefrom as the plunger is retracted from any of the chambers.

Any number of reagent storage chambers may be provided in combination with the reaction or test chamber, depending on the number of reagents to be delivered. Typically there will be a plurality, e.g. 2, 3 or 4, but possibly more, of reagents each to be delivered from its own respective storage chamber, which are preferably arranged symmetrically around and generally above the periphery of the reaction or test chamber. The volume of the or each storage chamber may independently be selected according to the volume of reagent which is required to be delivered from it.

The nature of the reagents included will be widely variable depending on the nature of the reaction being conducted. In addition to reactants necessary for carrying out the desired reaction, chambers containing calibration or quenching agents may be included, as these may also then be added at an appropriate point during the reaction.

As used in the context of this invention, the term "generally above" referring to the location of the reagent storage chamber(s) with respect to the reaction or test chamber means that the majority of the volume of the or each storage chambers lies above the level of the mouth of the reaction or test chamber, in other words such that liquid reagent can flow under gravity into the reaction or test chamber from the mouth of a storage chamber as it overflows therefrom when displaced by the plunger inserted therein. Generally it will preferably be the case that the total volume of each storage chamber will be positioned above the level of the mouth of the reaction or test chamber.

In order to achieve accurate dosing of reagents using the present invention, the shape and dimensions of the plunger element in combination with the shape and dimensions of the respective storage chambers will normally be predetermined, and the distance of travel of the plunger element into each chamber controlled by the plunger's control means. This will typically take into account typical amounts of residual reagent left in the various chambers or adhering to the outer surfaces of the chambers or the plunger element.

In practical implementations of this invention the plunger element is preferably arranged and controlled for insertion into, and retraction from, each storage chamber containing a reagent to be delivered, in a sequential manner. The plunger element may be in the form of a solid or hollow cylindrical rod or wand and the reagent storage chambers may typically be in the form of cylindrical supported tubes. In general, therefore, the plunger element is movable (a) along an upright (substantially vertical, preferably) axis, for the purpose of displacing liquid reagents from their respective storage chambers, and also for initially puncturing the seals which close them, and preferably also (b) in a perpendicular (substantially horizontal, preferably) plane, to allow it to be moved from one storage chamber to another, and so that it may be used (optionally also with or as an alternative to the aforesaid vertical motion) as a stirring rod for mixing reagents in the reaction or test chamber (or even the auxiliary reagent chamber therebeneath, if present). All these movements of the plunger element will be controllable in a predetermined manner by the aforementioned control means.

In versions of the apparatus in which the plunger is a hollow rod (preferably a hollow cylinder) this can be useful for enabling a retractable magnet to inserted into the plunger for the purpose of collecting sample-laden magnetic beads from an earlier stage of an assay apparatus of which the delivery apparatus of the invention forms a part. This is just one example of a known assay technique with which the invention may be used.

In one possible form of the discrete reaction or test unit according to the second aspect of the invention, the plunger element may itself be provided as a component of the unit, e.g. as a downwardly extending rod attached to an upper closure lid which seals the entire unit prior to use. In this case the lid part will preferably be provided with means by which it can be physically engaged by the plunger control means once it is disengaged from the unit. Also, for this case to be practically realisable, the distance between the lower tip of the plunger element and the lid part to which it is attached will preferably be greater than the depth of the various reagent storage chambers (and furthermore greater than the combined depths of the reagent storage chambers and the reaction or test chamber itself, in the case where there is an auxiliary reagent chamber therebeneath). In embodiments where the plunger element is carried on a lid as defined above, it may for example be expedient for the plunger to be mounted off-centre and the lid to form a carousel-like component for engagement by the plunger control means, whereby horizontal movement of the plunger between symmetrically arranged reagent chambers can be effected simply by rotation of the lid element.

Also encompassed by the present invention, according to a third aspect thereof, is a method for selectively delivering one or more liquid reagents into a reaction or test chamber in a test or assay apparatus, the method comprising:

providing the one or more liquid reagents in one or more respective storage chambers arranged generally above the reaction or test chamber; and inserting a plunger element into the mouth of a selected storage chamber so as to displace a selected reagent from therewithin into the reaction or test chamber generally therebelow by gravitational liquid overflow from the mouth of the chamber.

The above-defined method may in particular be practised in the use of a delivery apparatus, or a reaction, test or assay apparatus, or a discrete reaction or test unit, according to any embodiments of the first and second aspects of the invention discussed above.

Preferred embodiments of the present invention in its various aspects will now be described in detail, with reference to the accompanying drawings, in which.

Figure 1:
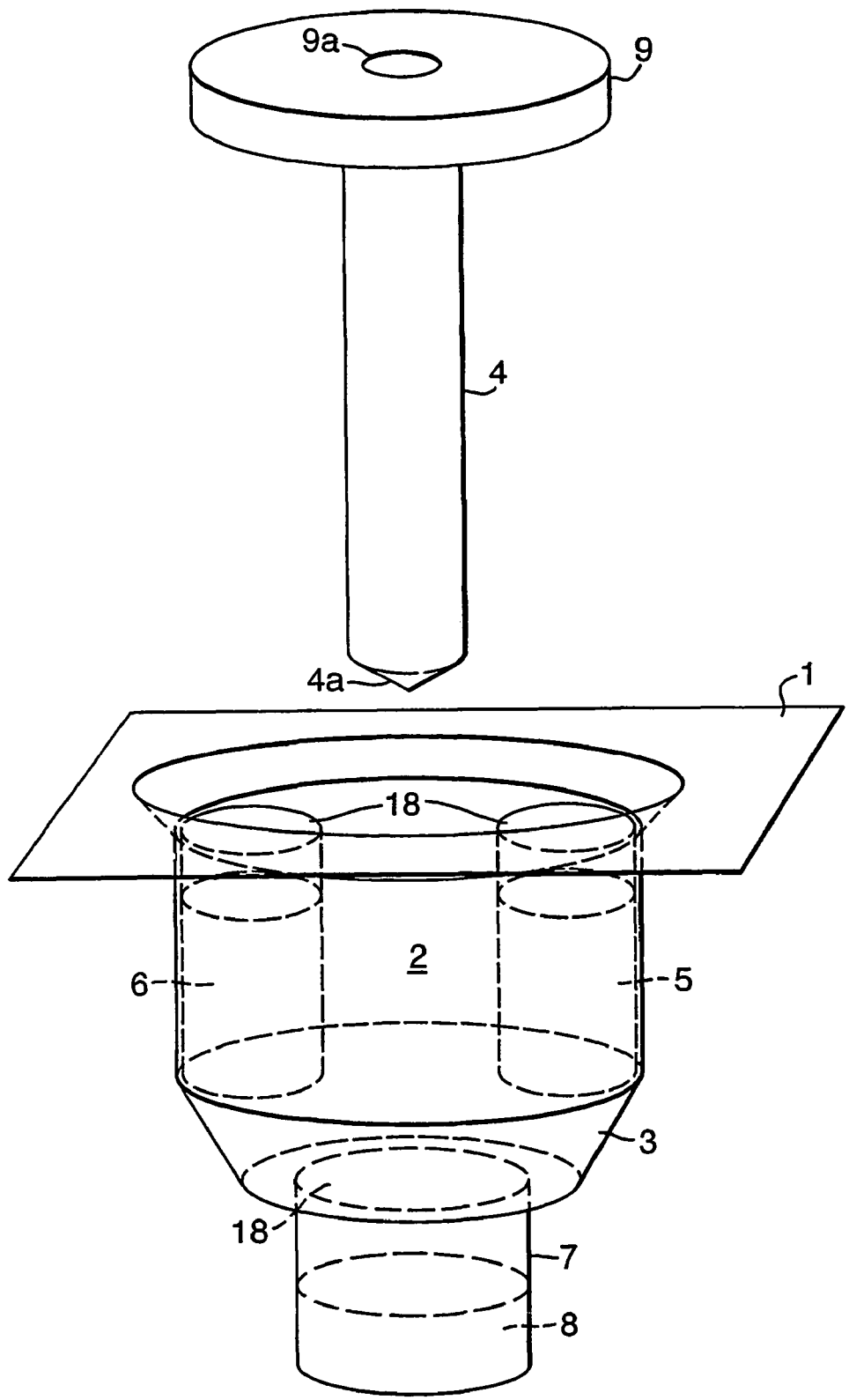
FIG. 1 is a schematic perspective view of an exemplary preferred embodiment of the reagent delivery apparatus of the invention.
Figure 6:
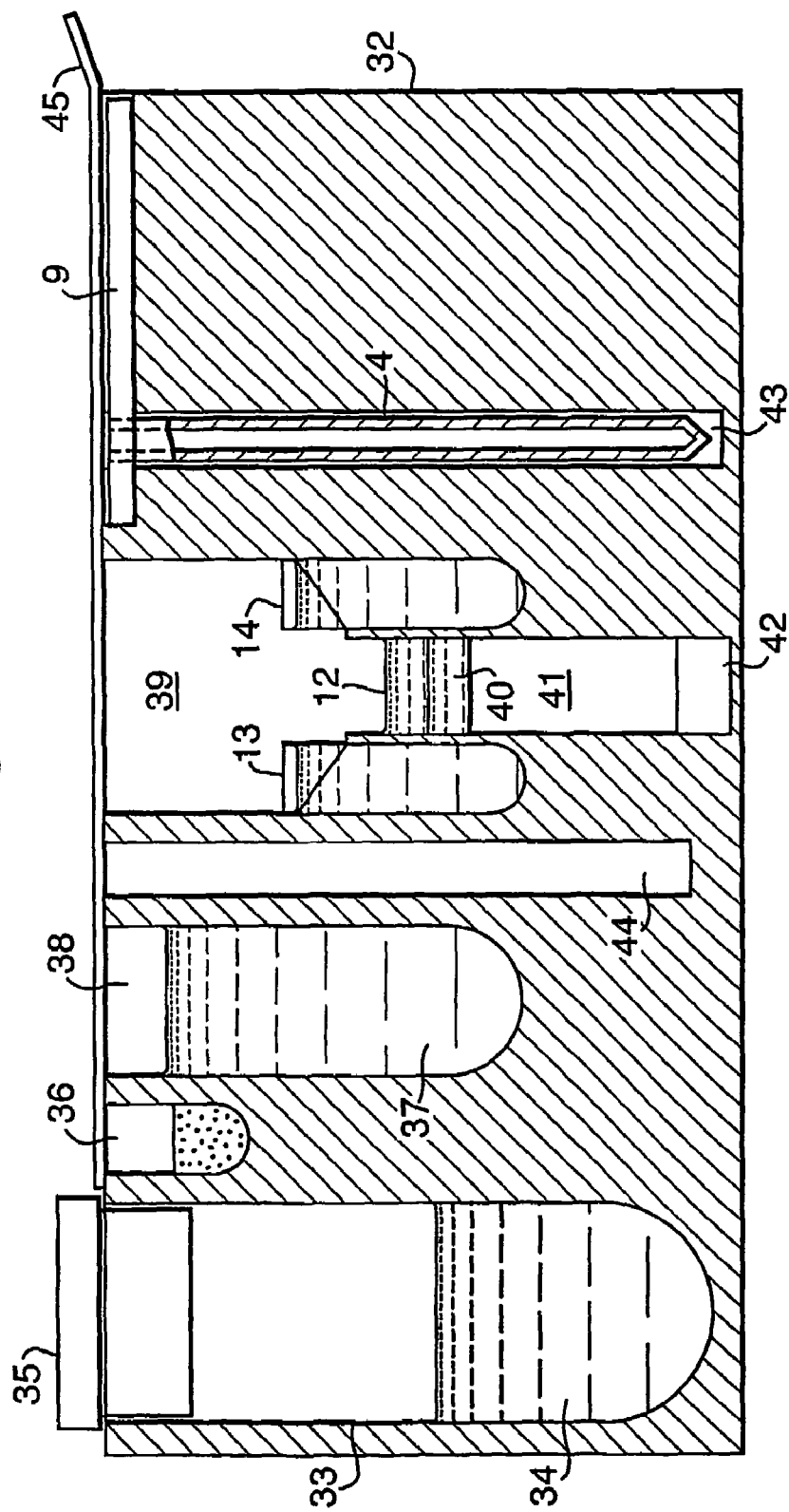

FIGS. 3(a) and 3(b) are schematic plan views of another embodiment of the apparatus, very similar to that of FIG. 1 but including four separate reagent storage chambers, showing schematically the unit respectively (a) before and (b) after the step of dispensing a first reagent into the reaction chamber of the apparatus;

FIGS. 4(a), (b) and (c) are schematic side views of a simplified version of the apparatus of FIG. 1 showing only two reagent storage chambers, respectively (a) at the start of the reagent delivery procedure, (b) part way through it with the first of the reagents in the process of being delivered into the reaction chamber, and (c) with the delivery of the first reagent completed and the plunger element ready for moving on to the next reagent chamber;

FIG. 5 illustrates a plunger element assembly which may be used in the apparatus of the invention, in which (a) is a perspective view showing a plunger with a magnet installed, (b) is a side view of the magnet, (c) and (d) are end and side views respectively of the plunger, and (e) is a top view of the assembly; and FIG. 6 is a diagrammatic view of an apparatus for conducting adenylate kinase assays incorporating the delivery apparatus of the invention.

Referring firstly to FIG. 1, housing 1 is formed from injection moulded polypropylene (which is a preferred material because it is readily autoclavable and because aqueous liquids do not so readily adhere to it, compared with nylon or polyethylene for example). The housing 1 contains a lower, central well or reaction chamber 2, which may be provided empty or may contain a pre-dispensed solid or liquid reagent 3 prior to use. A sample for reaction or analysis may be added to this chamber 2. A plunger 4 in the form of a solid rod or hollow wand with a sharp conical tip 4a is movable horizontally and vertically under the control of control hardware and software (not shown).

In this illustrated embodiment the top of the plunger 4 is formed as a lid 9 which may be used to seal the unit prior to use and/or for storage (as generally discussed earlier in this specification) and also for engagement (e.g. by means of slots (not shown) or any other suitable known attachment means in this type of hardware) by the mechanism which controls the movement of the plunger. Also in this embodiment the plunger 4 is shown as a hollow cylindrical rod having an open mouth 9a at the top for receiving a cylindrical magnet (30) (also under the overall control of the apparatus' control means).

Located above the reaction well 2 in a symmetrical fashion are two storage chambers 5,6 each containing a respective liquid reagent for delivery into the reaction well 2 at a predetermined point in the procedure and each sealed with a conventional foil seal 18. In the case of each reagent, when delivery is required, the plunger 4 is brought into register with the respective chamber 5 or 6, then lowered so as to puncture the respective seal 18 and then further inserted into the chamber so as to displace liquid reagent from therewithin, which simply overflows from the chamber and falls under gravity into the reaction well 2 therebelow.

Additional vertical, and/or possibly horizontal movements of the plunger or wand 4 in the reaction well 2 can be used to effect mixing of dispensed reagents with sample.

A separate, foil-sealed auxiliary chamber 7 is provided below the reaction chamber 2 to provide a means of storing one or more dried auxiliary reagents 8, which can be mixed with reagents in the reaction well by using the wand 4 to punch through its own respective protective seal 18.

In practice flow of reagents out of the various storage chambers down into the reaction well may be assisted by arranging for the surface tension of the various liquids to be lowered. This is a known technique in certain known analytical procedures and can be achieved for example by including either in the liquid reagents or possibly directly in the appropriate chambers of the apparatus a suitable amount of a surfactant such as Triton X-100 (trade mark).

Figure 2:
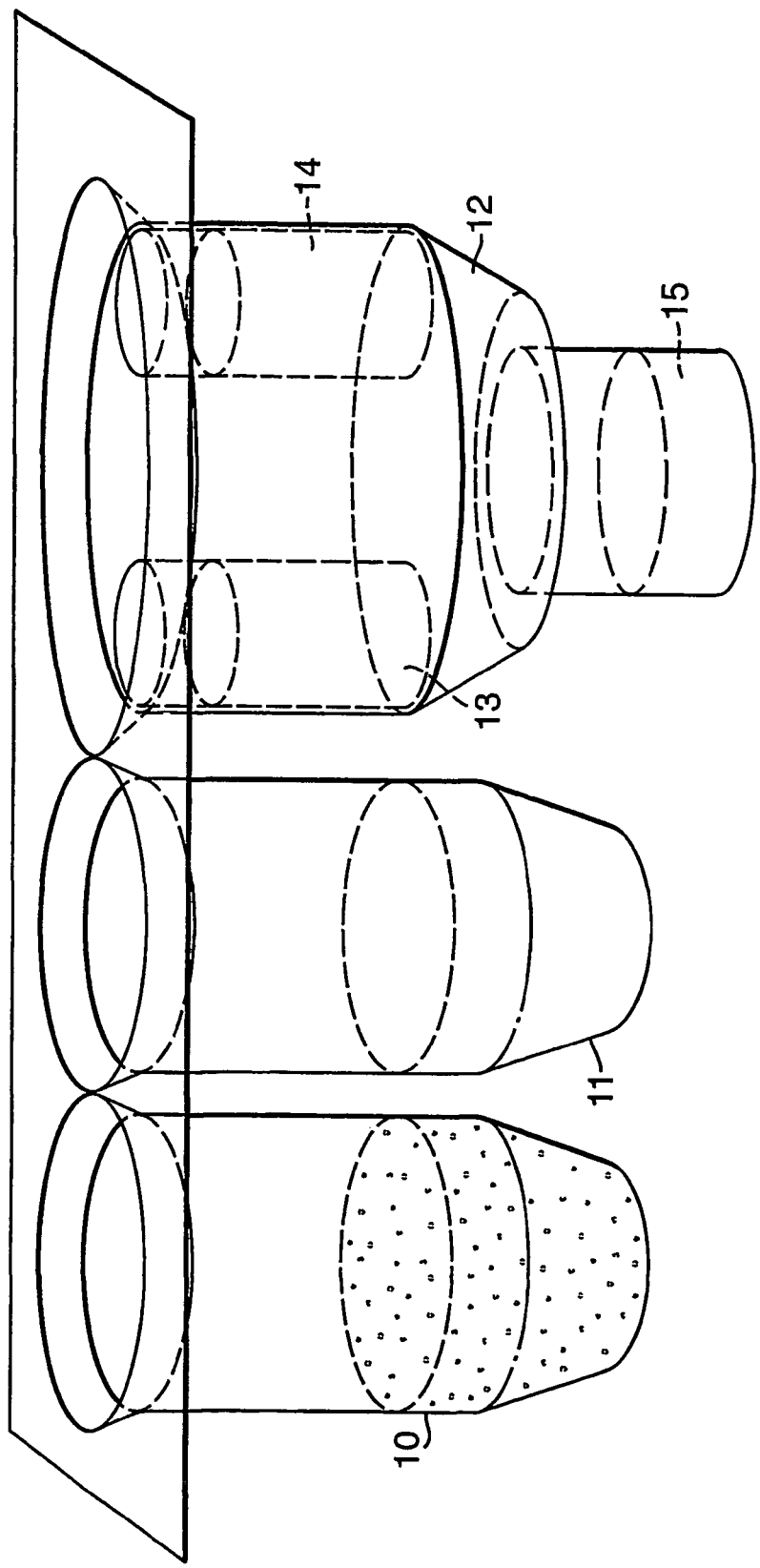
FIG. 2 is a schematic perspective view of the main elements of an exemplary assay apparatus into which the apparatus of FIG. 1 is incorporated.

FIG. 2 illustrates an example of an assay apparatus into which the delivery device of FIG. 1 is incorporated. By way of example, the unit of FIG. 1 is shown here as the final chamber in a series of three forming a disposable unit for carrying out AK-phage assays for detecting bacterial contamination of food.

The first stage well 10 will contain pre-dispensed magnetic beads, coated with antibodies, for specific capture of target organisms. Using a hollow plunger that can move from well to well, and that can accept a retractable magnet down its centre, beads plus captured bacterial cells may be transferred to the second stage well 11 containing pre-dispensed wash solution, and thence to the final chamber 12 of the unit of the invention for AK assay. As just one example, this first part of the assay may utilise a commercially available assay system called Kingfisher (trade mark), ex Labsystems. For the AK-phage endpoint detection, the reagent solutions in the final unit of the invention would typically be a nutrient broth 12 in the main reaction well or chamber, phage 13 in one of the storage chambers, ADP 14 in the other of the storage chambers and bioluminescence reagent 15 in the auxiliary chamber beneath the main reaction well.

The apparatus may suitably be calibrated by delivering a known amount of ATP from a storage well, in place of either the phage 13 or the ADP 14.

Additional reagents may be included in additional storage chambers or wells. For instance in the context of the AK-phage assay, it may be desirable to further include a well containing a quenching reagent, such as a bleach or an ink, which is able to halt the reaction or quench the bioluminescence therefrom. This is suitably arranged to be delivered at the end of the reaction.

This may be particularly helpful where the apparatus contains more than one test chamber and so can monitor multiple reactions sequentially. Quenching of a light reaction in one chamber will prevent light leakage, to the luminometer reading the signal from the subsequent reaction.

FIGS. 3(a) and 3(b) show another embodiment of the unit of the invention which is almost the same as that of FIG. 1 but instead having four reagent storage chambers 25, 26, 27 and 28. FIG. 3(a) illustrates the unit prior to the first reagent in chamber 25 being delivered into the reaction well 2, and FIG. 3(b) shows it afterwards, with the predetermined dose of first reagent 25" having been delivered into the reaction well 2, and leaving a residual amount 25' thereof behind in the chamber. FIGS. 4(a), (b) and (c) further illustrate, in simplified schematic form (but self-explanatorily to the skilled person from the foregoing descriptions and the annotations in the Figure) the operation of the apparatus of FIG. 1, with the reference numerals corresponding to the same identifying components and features as already referred to in the earlier Figures and discussed above.

FIG. 4(a) shows the apparatus at the start of the reagent delivery procedure. FIG. 4(b) shows the situation where the plunger 4 is about to be retracted from the reagent chamber 6 (in which a precalculated residual amount 6' of the reagent is left behind), having delivered a predetermined amount 6" of the, reagent from chamber 6 into the reaction well 2. FIG. 4(c) shows the situation, following on from FIG. 4(b) where the plunger 4 has been retracted from the storage chamber 6 and replaced in the central reaction well 2 and optionally moved vertically and/or horizontally to effect stirring of the contents of the reaction well 2.

FIG. 5 illustrates a particular form of plunger (4). In this embodiment, the lid 9 is rectangular in shape to fit the particular apparatus (see FIG. 6) in a sealing relationship in certain configurations as described hereinafter. In this case, it is further provided with additional grab holes (31) to allow the plunger assembly to be moved using a machine, from one chamber to another.

FIG. 6 illustrates a discrete apparatus, for conducting an adenylate kinase assay for the detection of bacterial cells. In this case, the delivery apparatus is incorporated into a support unit (32), which is provided with a series of additional wells. A first optional well (33) contains reagent broth (34), which may be required for dilution of viscous samples. It is closed by means of a cap (35). Adjacent this, is a well (36) which provides a store for magnetic beads which may be coated with a collection means such as antibodies for cells or microorganisms, and if required are specific for particular target cells or organisms. A broth wash liquid (37) is provided in a further adjacent well (38).

Reagent delivery apparatus in accordance with the invention, is included within the unit. In this embodiment, it comprises a chamber for holding phage (13) and a chamber for ADP (14). Nutrient broth (12) is supplied in a main reaction well (39) and freeze dried luciferin/luciferase reagent (40) is stored in a foil sealed auxiliary chamber (7), below the main reaction well (39). This unit is suspended above a well (41) containing buffer (42).

The plunger (4) as illustrated in FIG. 5 is accommodated within a further well (43). An additional well (44) is provided intermediate the well (37) and the reaction well (39) and is also able to accommodate the plunger (4), and is arranged so that when the plunger is in position in this well, the extended lid of the plunger (9) covers the reaction well (39).

Wells 36, 38, 39, 43 and 44 are sealed by means of a metal foil laminate sheet (45).

In use, a liquid or liquefied sample is placed in the sample well (33). For instance, samples may be formed by swilling a swab sample in nutrient broth (34) present in the well (33). The foil sheet (45) is then removed and a cylindrical magnet (30) (FIG. 5) is placed into the plunger (4), which is then used to collect magnetic beads from the well (36). The plunger (4) with the beads held magnetically on the surface is then immersed into a sample liquid. The magnet is (30) is removed, releasing the beads, which are then allowed to thoroughly mix with the sample, for example using the plunger (4) as a stirrer. During this time, cells will bind to the beads.

The magnet (30) is then replaced in the plunger (4) and so the beads become reattached to the plunger (4) which is removed from the sample. The beads are then deposited in the broth (12) in the reaction well (39) by placing the plunger (4) in the well, and removing the magnet (30). Phage (13), which is specific for the target cells, is added to the reaction mixture by pushing the plunger (4) into the chamber containing it, piercing the cover and causing the phage (13) to overflow into the main reaction well (39). The plunger (4) is then placed in the well (44) so that the lid (9) acts as a cover for the well (39).

The reaction mixture is then incubated for a sufficient period of time to allow the phage to lyse any target cells. Optionally at this stage, magnetic beads may be removed from the reagent well (39), using the plunger (4) with the magnet (30) inserted into it.

ADP (14) is then added to the reaction well by inserting the plunger (4) into the reaction chamber such that the ADP overflows into the reaction well (39). Again, the reaction may be allowed to incubate if necessary, with the plunger (4) in position in the well (44) so that the lid (9) closes the well (39), to allow adenylate kinase released to convert the ADP to ATP.

In a final stage ATP in the reaction well (39) is detected, by pushing the plunger (4) through the foil sealed chamber (7), releasing the dried luciferase and luciferin (40) and allowing these and the reaction mixture to flow into the buffer (42). The reagents will mix together and produce a bioluminescent signal, depending upon the amount of ATP present. This may be detected, for example using a luminometer. Any signal will be indicative that the target cells were present in the sample.

Intermediate each of these steps, the plunger (4) may be washed by immersion in the broth (37) in well (38). Movement of the plunger (4) is suitably effected automatically, for example using a computer controlled unit.

Thus the apparatus of the invention provides a convenient means of conducting complex assays.

The invention claimed is:

1. A reagent delivery system for selectively delivering one or more liquid reagents into a reaction or test chamber, the system comprising:
    a disposable unit comprising a reaction or test chamber,
    one or more storage chambers prefilled with the one or more liquid reagents, each of the one or more storage chambers having a closed bottom and an opening that is sealed by a protective puncturable seal, the opening of each storage chamber located above the reaction or test chamber; and
    a plunger element arranged and operable to puncture the protective seal, to be inserted into the opening of a selected storage chamber, and to displace a selected reagent from within the selected storage chamber into the reaction or test chamber located below the opening of the storage chamber, such that gravitational liquid overflow of the selected reagent from the opening of the selected storage chamber enters the reaction or test chamber.

2. A reaction system according to claim 1 wherein the one or more storage chambers are prefilled with one or more selected reagents in predetermined amounts.

3. A reaction system according to claim 1, wherein the protective puncturable seal closing each of the chambers is breakable or perforatable by the tip of the plunger element as the plunger moves into a respective chamber's opening.

4. A reaction, test or assay apparatus comprising a reagent delivery system according to claim 1, together with control means for controlling physical movement of the plunger element.

5. A reaction, test or assay apparatus according to claim 4 which is an apparatus for detecting or assaying bacterial contamination of food, or an apparatus for extracting and purifying DNA.

6. A reaction, test or assay apparatus according to claim 4 which further comprises heating means for the reaction or test chamber and/or the storage chamber(s).

7. A reaction, test or assay apparatus according to claim 6 wherein the heating means comprises an electrically conducting polymer, which is heatable by means of a controlled electric current.

8. An apparatus according to claim 4, wherein the plunger element is arranged and controllable for insertion into and retraction from each storage chamber containing a reagent to be delivered, in a sequential manner.

9. An apparatus according to claim 4, wherein the plunger element is in the form of a solid or hollow cylindrical rod or wand and the one or more reagent storage chambers are in the form of supported cylindrical tubes.

10. An apparatus according to claim 4, wherein the plunger element is movable both along a substantially vertical axis and in a substantially horizontal plane.

11. An apparatus according to claim 4, wherein the plunger element is in the form of a hollow rod for accommodating therein a retractable magnet.

12. An apparatus according to claim 4, wherein the plunger element is formed as a downwardly extending rod attached to an upper closure lid which seals the delivery apparatus prior to use, the lid incorporating means by which it can be physically engaged by plunger control means once it is disengaged from the apparatus.

13. A reagent delivery system for selectively delivering one or more liquid reagents into a reaction or test chamber, the system comprising:
    a disposable unit comprising a reaction or test chamber;
    one or more storage chambers prefilled with the one or more liquid reagents,
    the one or more storage chambers having closed bottoms and openably sealed mouths which mouths are arranged above the reaction or test chamber; and
    a plunger element arranged and operable for insertion into the mouth of a selected storage chamber so as to displace a selected reagent from therewithin into the reaction or test chamber generally therebelow by gravitational liquid overflow from said mouth of the selected storage chamber,
    wherein the plunger element is formed as a downwardly extending rod attached to an upper closure lid which seals the delivery apparatus prior to use,
    wherein the plunger is mounted off-centre on the lid and the lid forms a carousel-like component for engagement by a plunger control means, whereby horizontal movement of the plunger between symmetrically arranged reagent chambers is effected by rotation of the lid.

14. A disposable reaction or test unit for use in a reaction system according to claim 1, the unit comprising a reaction or test chamber, and one or more storage chambers for containing the one or more liquid reagents, wherein the one or more storage chambers have closed bottoms and open mouths which mouths are arranged above the reaction or test chamber.

15. A reaction or test unit according to claim 14, wherein the reaction or test chamber and the one or more storage chambers are contained within a moulded plastics housing.

16. A reaction or test unit according to claim 14, wherein the reaction or test chamber and the one or more storage chambers are of moulded polypropylene.

17. A reaction or test unit according to claim 15, wherein the housing includes an upper peripheral wall which collectively surrounds and extends upwardly past the mouths of the storage chamber(s) in order to act as a baffle to direct liquid reagent(s) overflowing from the chamber(s) into the reaction or test chamber therebelow.

18. A reagent delivery system for selectively delivering one or more liquid reagents into a reaction or test chamber, the system comprising:
    a disposable unit comprising a reaction or test chamber,
    one or more storage chambers prefilled with the one or more liquid reagents,
    the one or more storage chambers having closed bottoms and openably sealed mouths which mouths are arranged above the reaction or test chamber; and
    a plunger element arranged and operable for insertion into the mouth of a selected storage chamber so as to displace a selected reagent from therewithin into the reaction or test chamber generally therebelow by gravitational liquid overflow from said mouth of the selected storage chamber,
    further comprising, below the reaction or test chamber, an auxiliary reagent chamber containing a predispensed amount of an auxiliary liquid or solid reagent into which the contents of the reaction or test chamber are deliverable at a desired stage in a reaction or test procedure, the mouth of the auxiliary reagent chamber being sealed with its own protective sealing means which defines the bottom of the reaction or test chamber prior to use.

19. A reagent delivery system for selectively delivering one or more liquid reagents into a reaction or test chamber, the system comprising:

a disposable unit comprising a reaction or test chamber;

a plurality of reagent storage chambers prefilled with the one or more liquid reagents, the plurality of reagent storage chambers having closed bottoms and openably sealed mouths which mouths are arranged above the reaction or test chamber; and a plunger element arranged and operable for insertion into the mouth of a selected storage chamber so as to displace a selected reagent from therewithin into the reaction or test chamber generally therebelow by gravitational liquid overflow from said mouth of the selected storage chamber, wherein the reagent storage chambers are arranged symmetrically around and generally above the periphery of the reaction or test chamber.

20. A reaction or test unit according to claim 6 wherein the test chamber and/or storage chamber(s) further comprise heating means.

21. A reaction or test unit according to claim 20 wherein the heating means comprises an electrically conducting polymer.

22. A reaction or test unit according to claim 21 wherein the electrically conducting polymer is in intimate contact with the test chamber and/or storage chamber(s).

23. A reaction or test unit according to claim 21 wherein the electrically conducting polymer is integral with the test chamber and/or storage chamber.

24. A reaction or test unit according to claim 23 wherein the electrically conducting polymer is overmoulded into a portion of the test chamber and/or storage chamber.

25. A method for carrying out a chemical reaction, comprising selectively delivering one or more liquid reagents into a reaction or test chamber in a test or assay apparatus, the method comprising:

providing the one or more liquid reagents in one or more respective storage chambers, each storage chamber having a closed bottom and an opening that is sealed by a protective puncturable seal, the opening of each storage chamber arranged generally above the reaction or test chamber; and inserting a plunger element into the opening of a selected storage chamber so as to puncture the protective seal and displace a selected reagent within the selected storage chamber into the reaction or test chamber located below the opening of the storage chamber, such that gravitational liquid overflow of the selected reagent from the opening of the selected storage chamber enters the reaction or test chamber.

* * * * *